(12) United States Patent
Miyazawa et al.

(10) Patent No.: US 12,332,208 B2
(45) Date of Patent: Jun. 17, 2025

(54) SENSOR CHIP, SENSING APPARATUS, COVER, BODY FLUID COLLECTION DEVICE, AND SENSOR

(71) Applicant: PROVIGATE INC., Tokyo (JP)

(72) Inventors: Yuuya Miyazawa, Tokyo (JP); Narushi Ito, Tokyo (JP); Norikazu Katayama, Tokyo (JP); Mitsumi Nishi, Tokyo (JP); Yoshiyuki Yanagimoto, Tokyo (JP)

(73) Assignee: PROVIGATE INC., Tokyo (JP)

( * ) Notice: Subject to any disclaimer, the term of this patent is extended or adjusted under 35 U.S.C. 154(b) by 482 days.

(21) Appl. No.: 17/041,937

(22) PCT Filed: Mar. 29, 2019

(86) PCT No.: PCT/JP2019/014040
§ 371 (c)(1),
(2) Date: Sep. 25, 2020

(87) PCT Pub. No.: WO2019/189777
PCT Pub. Date: Oct. 3, 2019

(65) Prior Publication Data
US 2021/0048404 A1  Feb. 18, 2021

(30) Foreign Application Priority Data
Mar. 30, 2018 (JP) ................. 2018-067742

(51) Int. Cl.
*G01N 27/327* (2006.01)
*B01L 3/00* (2006.01)
*G01N 1/10* (2006.01)

(52) U.S. Cl.
CPC .... *G01N 27/3273* (2013.01); *B01L 3/502715* (2013.01); *G01N 1/10* (2013.01); *B01L 2300/0645* (2013.01); *B01L 2300/161* (2013.01)

(58) Field of Classification Search
CPC .......................... G01N 27/3273; G01N 1/10; B01L 3/502715; B01L 2300/0645;
(Continued)

(56) References Cited

U.S. PATENT DOCUMENTS

| 6,120,676 A | 9/2000 | Heller et al. |
| 6,143,164 A | 11/2000 | Heller et al. |

(Continued)

FOREIGN PATENT DOCUMENTS

| JP | H06300729 A | 10/1994 |
| JP | H11271260 A | 10/1999 |

(Continued)

OTHER PUBLICATIONS

International Search Report for Application No. PCT/JP2019/014040 mailed Jul. 2, 2019.
(Continued)

*Primary Examiner* — Jill A Warden
*Assistant Examiner* — Alex Ramirez
(74) *Attorney, Agent, or Firm* — McBee, Moore & Vanik IP, LLC

(57) ABSTRACT

A sensor chip (30), to be brought close to an organism to collect a body fluid in order to chemically measure the body fluid, is configured such that a surface (100) to be brought close to the organism is curved.

9 Claims, 15 Drawing Sheets

(58) Field of Classification Search
CPC ........... B01L 2300/161; A61B 5/14517; A61B
5/1477; A61B 5/1451; A61B 5/6821;
A61B 2010/0067; A61B 2560/0443;
A61B 2562/0295; A61B 5/150358; A61B
5/157; A61B 5/150022; A61B 5/14532
See application file for complete search history.

(56) References Cited

U.S. PATENT DOCUMENTS

| | | | |
|---|---|---|---|
| 6,551,494 B1 | 4/2003 | Feldman et al. | |
| 6,576,101 B1 | 6/2003 | Heller et al. | |
| 8,880,139 B1 | 11/2014 | Etzkorn et al. | |
| 2003/0201194 A1 | 10/2003 | Heller et al. | |
| 2003/0211625 A1 | 11/2003 | Cohan | |
| 2004/0055898 A1 | 3/2004 | Feldman et al. | |
| 2005/0008537 A1 | 1/2005 | Mosoiu et al. | |
| 2005/0013731 A1 | 1/2005 | Burke et al. | |
| 2005/0016844 A1 | 1/2005 | Burke et al. | |
| 2005/0069925 A1 | 3/2005 | Ford et al. | |
| 2005/0164322 A1 | 7/2005 | Heller et al. | |
| 2006/0212021 A1* | 9/2006 | Yazaki | A61B 5/15117 604/500 |
| 2007/0208309 A1 | 9/2007 | Flora et al. | |
| 2008/0017522 A1 | 1/2008 | Heller et al. | |
| 2008/0194990 A1 | 8/2008 | Heller et al. | |
| 2008/0277291 A1 | 11/2008 | Heller et al. | |
| 2008/0277292 A1 | 11/2008 | Heller et al. | |
| 2008/0277293 A1 | 11/2008 | Heller et al. | |
| 2008/0277294 A1 | 11/2008 | Heller et al. | |
| 2008/0318261 A2 | 12/2008 | Heller et al. | |
| 2009/0000960 A1 | 1/2009 | Heller et al. | |
| 2009/0000961 A1 | 1/2009 | Heller et al. | |
| 2009/0002683 A1 | 1/2009 | Feldman et al. | |
| 2009/0078586 A1 | 3/2009 | Heller et al. | |
| 2009/0151864 A1 | 6/2009 | Burke et al. | |
| 2009/0162532 A1 | 6/2009 | Mosoiu et al. | |
| 2010/0012510 A1 | 1/2010 | Heller et al. | |
| 2010/0012511 A1 | 1/2010 | Heller et al. | |
| 2010/0012512 A1 | 1/2010 | Feldman et al. | |
| 2010/0012513 A1 | 1/2010 | Heller et al. | |
| 2010/0012514 A1 | 1/2010 | Feldman et al. | |
| 2010/0012515 A1 | 1/2010 | Feldman et al. | |
| 2010/0012527 A1 | 1/2010 | Feldman et al. | |
| 2010/0012528 A1 | 1/2010 | Feldman et al. | |
| 2010/0018867 A1 | 1/2010 | Feldman et al. | |
| 2010/0018868 A1 | 1/2010 | Heller et al. | |
| 2011/0000610 A1 | 1/2011 | Burke et al. | |
| 2011/0011738 A1 | 1/2011 | Burke et al. | |
| 2012/0009095 A1 | 1/2012 | Burke et al. | |
| 2012/0010486 A1 | 1/2012 | Fujiwara | |
| 2012/0088258 A1 | 4/2012 | Bishop et al. | |
| 2013/0220838 A1 | 8/2013 | Fujiwara | |
| 2014/0353173 A1 | 12/2014 | Heller et al. | |
| 2016/0074019 A1 | 3/2016 | Hata et al. | |
| 2016/0123916 A1 | 5/2016 | Heller et al. | |
| 2016/0153926 A1 | 6/2016 | Fujiwara | |
| 2017/0248573 A1* | 8/2017 | Sullivan | G01N 13/04 |
| 2018/0059105 A1* | 3/2018 | Lowe | G01N 33/54366 |

FOREIGN PATENT DOCUMENTS

| | | |
|---|---|---|
| JP | 2000509507 A | 7/2000 |
| JP | 2004020465 A | 1/2004 |
| JP | 2004237089 A | 8/2004 |
| JP | 2005087117 A | 4/2005 |
| JP | 2006000521 A | 1/2006 |
| JP | 2007524821 A | 8/2007 |
| JP | 2007-526440 A | 9/2007 |
| JP | 2016200430 A | 12/2016 |
| WO | 2007111084 A1 | 10/2007 |
| WO | 2010116624 A1 | 10/2010 |
| WO | 2017039976 A1 | 3/2017 |
| WO | 2017179919 A1 | 10/2017 |
| WO | WO-2018067412 A1 * | 4/2018 ......... A61B 10/0045 |

OTHER PUBLICATIONS

Supplementary European Search Report for Application No. EP 19776136 mailed Nov. 23, 2021.
Chinese Office Action from CN201980023841.5 dated Oct. 10, 2022.

* cited by examiner

SENSOR CHIP, SENSING APPARATUS, COVER, BODY FLUID COLLECTION DEVICE, AND SENSOR

CROSS-REFERENCE TO RELATED APPLICATIONS

This application is the National Stage entry of International Application No. PCT/JP2019/014040, filed 29 Mar. 2019, which claims priority to Japanese Patent Application No. 2018-067742, filed 30 Mar. 2018.

BACKGROUND

Field

The present disclosure relates to a sensor chip, a sensing device, a cover, a body fluid collection device, and a sensor.

Description of Related Art

In recent years, sensor chips for detecting various substances contained in body fluids have been developed. As an example, a glucose sensor for detecting glucose in blood has been developed.

SUMMARY OF INVENTION

Technical Problem

The inventors of the present application investigated sensor chips that can detect not only glucose in blood but also various substances (including glucose) contained in body fluids other than blood (e.g., tears). There is also a need for high sensitivity sensors for various electrochemical measurements for body fluids. To this end, the inventors of the present application have investigated novel structures of sensor chips and related techniques.

Solution to Problem

According to one embodiment of the present disclosure, a sensor chip is provided, to be brought in close proximity to a living body for collecting body fluids (or bodily fluids), and for measuring chemical substances in the body fluids, wherein the surface to be brought in close proximity to the living body is configured a curved surface.

According to another embodiment of the present disclosure, a sensor chip is provided, to be brought in close proximity to a living body for collecting body fluids (or bodily fluids), and for measuring chemical substances in the body fluids, the sensor chip comprising: a body fluid collection unit having a surface configured with a curved surface to be brought in close proximity to a living body and having a body fluid collection port for collecting the body fluid; and a sensing unit for performing a chemical measurement on the body fluid collected by the body fluid collection unit.

According to another embodiment of the present disclosure, a sensor chip is provided, to be brought in close proximity to a living body for collecting body fluids (or bodily fluids), and for performing an electrochemical measurement on the body fluids, the sensor chip comprising: a body fluid collection unit having a surface configured with a curved surface to be brought in close proximity to a living body and having a body fluid collection port for collecting the body fluid; a sensing unit for performing an electrochemical measurement on the body fluid collected by the body fluid collection unit; and an electrical measuring unit for receiving an analog electrical signal from the sensing unit and outputting a digital signal.

According to another embodiment of the present disclosure, a sensor chip is provided, to be brought in close proximity to a living body for collecting body fluids (or bodily fluids), and for performing an electrochemical measurement on the body fluids, the sensor chip comprising: a body fluid collection unit having a surface configured with a curved surface to be brought in close proximity to a living body and having a body fluid collection port for collecting the body fluid; a sensing unit for performing an electrochemical measurement on the body fluid collected by the body fluid collection unit; an electrical measuring unit for receiving an analog electrical signal from the sensing unit and outputting a digital signal; and a housing.

In accordance with another aspect of the present disclosure, a cover is provided for use, to be brought in close proximity to a living body for collecting body fluids (or bodily fluids), and for performing a chemical measurement on bodily fluids, the cover comprising a surface configured with a curved surface to be brought in close proximity to a living body.

In accordance with another aspect of the present disclosure, a device is provided, to be brought in close proximity to a living body for collecting body fluids, wherein the surface to be brought in close proximity to the living body is configured by a curved surface.

In accordance with another aspect of the present disclosure, a sensor is provided, for electrochemical measurement of a liquid, the sensor comprising: a counter electrode configured to contact the liquid; a working electrode configured to contact the liquid; and a reference electrode configured to contact the liquid and disposed between the counter electrode and the working electrode.

Advantageous Effects of Invention

According to one embodiment of the present disclosure, a sensor chip having a novel structure and related techniques is provided.

BRIEF DESCRIPTION OF DRAWINGS

The objects described above, and other objects, features, and advantages will become further apparent from the preferred embodiments described below and the accompanying drawings.

DETAILED DESCRIPTION OF A PREFERRED EMBODIMENT

Figure 1:
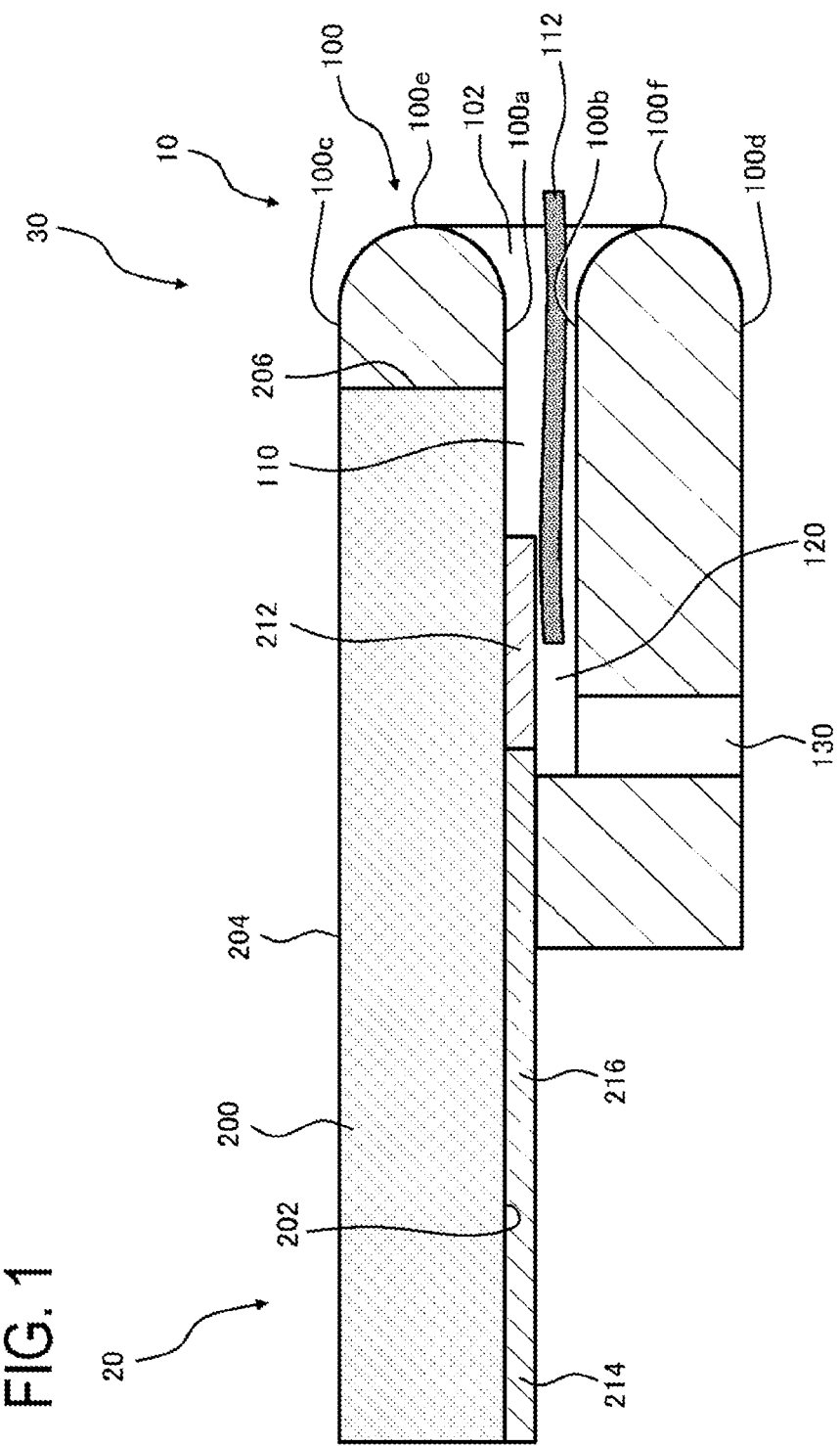
FIG. 1 illustrates a cross-sectional view of a sensor chip according to one embodiment.

A portion of a living body to which a "surface to be brought in close proximity to a living body" is brought in close proximity according to the present disclosure may be an outer skin of a living body, may be an epidermis, or may be an epithelium. The outer skin or the like of the living body may be the skin, epidermis or mucous membrane of an animal. The animal may be a human. Preferably, the body fluid collection device of the present disclosure is formed so as not to cause substantial damage or pain when in contact with the surface of the living body. In some embodiments, body fluids may collect body fluids from organs in the body. The portion of a living body to which a "surface in close proximity to the living body" is brought in close proximity may be a surface of an organ or an internal organ which appears by incision or the like, or may be a tissue surface inside thereof. In another embodiment, a medical device or a device or the like may be inserted into a living body to reach a predetermined portion in the body to collect body fluids, without incision.

A "living body" may be an animal, a mammal, or a human.

The solution may be a body fluid, a solution derived from a body fluid, and may be a diluted solution of a body fluid. The solution may be a solution that is not a body fluid (not derived from a body fluid), and may be a mixture of a solution derived from a body fluid or a body fluid and a solution not derived from a body fluid. The solution may be a solution used for sample measurement and may be a solution used for measurement for calibration. For example, the solution may be a standard or reference solution or a calibration solution.

The "body fluid" may be lymph fluid, tissue fluid such as interstitial fluid, intercellular fluid, interstitial fluid, and the like, and may be body cavity fluid, serosal fluid, pleural fluid, ascites fluid, pericardial effusion, cerebrospinal fluid, joint fluid (synovial fluid), and aqueous humor of the eye (aqueous humor). The body fluid may be digestive fluid such as saliva, gastric juice, bile, pancreatic juice, intestinal fluid, etc., and may be sweat, tears, nasal mucus, urine, semen, vaginal fluid, amniotic fluid, milk, etc. "Body fluid" may be a solution. The solution may contain a physiological buffer such as phosphate buffered saline (PBS) or N-tris(hydroxymethyl)methyl-2-aminoethanesulfonic acid buffer (TES).

The solution may contain a substance to be measured. For example, the solution may be tears and the substance to be measured may be glycoalbumin (glycated albumin) contained in tears. Alternatively, the measurement object may be glucose, lactate, albumin, glycoalbumin (glycated albumin), uric acid, glycated hemoglobin in blood or serum, glucose in interstitial fluid, glucose, albumin in tears, albumin or glycoalbumin (glycated albumin), glucose in urine, etc.

The "surface to be brought in close proximity to a living body" may be a surface to come in contact with the epidermis of the living body, and may be a surface configured to sufficiently approach the epidermis of the living body so as to be able to collect the body fluid. In some embodiments, a "surface to be brought in close proximity to a living body" may be configured to come in contact with a body fluid. A "surface to be brought in close proximity to a living body" may come close to a living body in a portion thereof and may come close in its entirety.

The measurement of the chemical may be an electrochemical measurement. "Chemical measurement of a body fluid" may be a measurement such as detecting or quantifying a substance contained in or dissolved in a body fluid (a substance to be measured).

"Measurement of a chemical substance" may be an electrochemical measurement and may be a non-electrochemical measurement. As an example of electrochemical measurement, "measurement of chemicals" may be a potentiometric measurement, a current measurement (amperometry), a three-electrode method, or an impedance measurement. As an example of non-electrochemical measurements, the "measurement of chemicals" may be a photodiode or photon counter measurement that detects light changes, exothermic measurements (calorimetry), surface acoustic wave measurements that detect weight changes, or surface plasmon resonance. "Measurement of a chemical substance" may be a combined plurality of measurements of electrochemical measurements, non-electrochemical measurements, and other measurements including exemplifications described above.

In the present disclosure, a "curved surface" may be a curved surface defined by one curvature or one radius of curvature, may be a curved surface having a different curvature at each point of the curved surface, may be a curved surface defined by a plurality of curvatures or radii of curvature, or may consist of a combination of curvatures that cannot be counted. In some embodiments, the curvature on the surface may be continuous (continuous curvature).

The radius of curvature may be greater than or equal to 0.5 mm. The radius of curvature may be greater than or equal to 0.1 mm, 0.2 mm, 0.35 mm, 0.5 mm, 0.8 mm, 1.0 mm, 1.5 mm, 3 mm, 5 mm, 10 mm, etc. The curvature may be smaller than or equal to 2 $mm^{-1}$. If the radius of curvature exceeds 0.2 mm, it is considered that the fear feeling of the living body is likely to be reduced. If the radius of curvature is 0.35 mm or greater, it is considered that the possibility of damaging can be reduced even if it comes into contact with a living body. If the radius of curvature is 0.5 mm or greater, it is considered that the possibility of giving a sense of security to the living body can be increased. The relationship between the radius of curvature and the damage to the living body, fear, and sense of security described above is merely an example, and other correlations may be possible. The curvature may be smaller than or equal to a value such as 10 $mm^{-1}$, 5 $mm^{-1}$, 3 $mm^{-1}$, 2 $mm^{-1}$, 1.25 $mm^{-1}$, 1 $mm^{-1}$, 0.67 $mm^{-1}$, 0.33 $mm^{-1}$, 0.2 $mm^{-1}$, 0.1 $mm^{-1}$, and may be smaller than or equal to such. Theoretically, it is considered that there is no particular maximum value or minimum value of curvature in the radius of curvature. Surfaces with greater radius of curvature or smaller curvature can avoid or reduce possible damage to the epidermis or epithelium, such as the skin, or pain to the living body.

The surface roughness of the surface to be brought in close proximity to the living body may be 1 μm (micrometer, the same applies hereafter) Ra (arithmetic mean roughness, the same applies hereafter). If the surface roughness is 0.1 μmRa or smaller, it is considered that the resistance feeling to the living body can be further lowered and a smooth feeling can be given, relatively regardless of the influence of the material. Even if the surface roughness is 0.1 μm Ra or larger, it is considered that the possibility of giving a sense of resistance to the living body can be reduced by selecting the hardness of the material. The above-mentioned correlations between the surface roughness and the sensation or feeling given to the living body are merely examples, and there may be other correlations.

The surface roughness of the surface to be brought in close proximity to the living body may be 6 μmRy or Rz (maximum height, the same applies hereinafter). If the surface roughness is 0.6 μmRy or Rz or smaller, the resistance feeling given to the living body can be further reduced and it can give a smooth feeling, relatively regardless of the influence of the material. Even if the surface roughness is 6 μmRy or Rz or more, by selecting the hardness of the material, it is considered possible to reduce the possibility of giving a sense of resistance to living body. The above-mentioned correlations between the surface roughness and the sensation given to the living body are merely examples, and there may be other correlations.

Embodiments of the present disclosure will be described with reference to the accompanying drawings.

FIG. 1 illustrates a cross-sectional view of the sensor chip 30 according to an embodiment. FIG. 1 illustrates a cross-section along an extending direction of a flow path 110, which will be described later.

As shown in FIG. 1, in one embodiment, a surface 100 to come in close proximity to a living body is constructed of a curved surface in a sensor chip 30 to be brought in close proximity of a living body, for collecting body fluids and performing chemical measurement of body fluids. In the example illustrated in FIG. 1, the sensor chip 30 has a surface 100 which is formed of a curved surface and which is brought close to the living body. In another embodiment, in a body fluid collection device that is brought in close proximity to a living body and to collect body fluids, a surface to be brought in close proximity to the living body may be configured with a curved surface.

The sensor chip 30 shown in FIG. 1 includes a body fluid collection port 102. The body fluid collection port 102 may be disposed within a surface 100 to be brought in close proximity to the living body, or may be surrounded by a surface 100 to be brought in close proximity to the living body.

In some embodiments, the opening of the body fluid collection port 102 may be formed of a curved surface. The opening of the body fluid collection port 102 may be defined as a second curved surface. In this case, the surface that is brought in close proximity to the living body, other than the opening, may be defined as the first curved surface.

The radius of curvature of the curved surface of the opening of the body fluid collection port 102 may be greater than or equal to 0.5 mm may be greater than or equal to 1.0 mm, 1.5 mm, 2 mm, 2.5 mm, 3 mm, or the like. The curvature of the curved surface of the opening of the body fluid collection port may be 2 $mm^{-1}$ or smaller. Curvature may be smaller than or equal to a value such as 1 $mm^{-1}$, 0.67 $mm^{-1}$, 0.5 $^{-1}$, 0.4 $mm^{-1}$, 0.33 $mm^{-1}$ and the like. The curvatures of the first curved surface and the second curved surface may be continuous.

In some embodiments, the opening of the body fluid collection port 102 may be formed as an opening of a through hole to the sensor chip 30. In other embodiments, it may be formed in a form of a notch at an end of a surface to be brought in close proximity to a living body, of the sensor chip 30.

In other embodiments, the opening of the body fluid collection port 102 may not be curved.

In some embodiments, the opening may be a resilient (or elastic) material. An opening comprising or consisting of a substantially elastic material may elastically deform when contacted or pressed against a living body, which can avoid or reduce damage or the like to the living body. In this case, the opening of the body fluid collection port 102 may not have a curved shape. For example, the elastic material may be silicone, may be a rubber material, and may be a low hardness polymeric material. The elastic material may be a polymeric material and may be a non-polymeric material. The elastic material may be a material having a low hardness (having a hardness of about 30 degrees or less according to a durometer (hardness tester)), a material having a general hardness (having a hardness of about 40 degrees to 60 degrees according to a durometer), or a material having a high hardness (having a hardness of about 70 degrees to 80 degrees according to a durometer).

The sensor chip 30 includes a body fluid collection unit 10 and a sensing unit 20. The body fluid collection unit 10 has a surface 100 and a body fluid collection port 102. The sensing unit 20 performs chemical measurements on the body fluid collected at the body fluid collection port 102. The body fluid collection unit 10 and the sensing unit 20 may be integrally formed and may be configured to be mechanically, physically, or chemically connected. The body fluid collection unit 10 and the sensing unit 20 may be coupled to each other in a fitting manner and may be removable from each other. The body fluid collection unit 10 and the sensing unit 20 may be bonded to each other.

The body fluid collection unit 10 has a fluid channel (or flow path) 110. The fluid channel 110 fluidly connects the body fluid collection port 102 to the sensing unit 20. In some embodiments, the fluid channel 110 may be a through-hole penetrating the body fluid collection unit 10, or may be a slit formed on the surface 100, or may be formed by combining the through-hole and the slit. In some embodiments, one fluid channel 110 may be formed per fluid collection unit 10, or a plurality of channels 110 may be formed.

The fluid channel 110 through which the body fluid or solution passes may be hydrophilic on at least a portion of its surface. Hydrophilic surfaces may facilitate movement and delivery of body fluids and the like in the fluid channel 110.

Hydrophilicity may be a state of a surface in which a body fluid or solution proceeds in a fluid channel 110 or the like at such a rate that a time at which the body fluid or solution reaches the surface of the site to be contacted does not substantially affect the target chemical measurement. In some embodiments, a hydrophilic property may be a state of a surface having a contact angle of 90 degrees, 60 degrees, 45 degrees, 20 degrees, 10 degrees, or 5 degrees or less, of a liquid having the same properties as the body fluid or solution to be measured. In general, it is considered that the smaller the contact angle, the higher the rate of collection of bodily fluid into the fluid channel.

In some embodiments, a hematocrit capillary tube may be inserted or positioned in the channel 110. In some embodiments, the fluid collection unit 10 may be provided with a hematocrit capillary in the channel 110. In some embodiments, the fluid channel 110 is a through-hole, and a hematocrit capillary tube may be inserted into the through-hole.

A hematocrit tube disposed in the body fluid collection unit 10 may be non-protruding outwardly from the body fluid collection port 102 at one end thereof, or may be contained in the through hole of the body fluid collection unit 10 over the entire length. By placing the end of the hematocrit capillary tube in the body fluid collection unit (sensor chip 30), damage to the living body due to the end of the hematocrit tube can be reduced when the body fluid collection port 102 comes close to or in contact with the living body.

In other embodiments, the surface of at least a portion of the fluid channel 110 may be coated with a hydrophilic thin film, or may be hydrophilized by surface treatment such as UV or plasma treatment. By applying a hydrophilic treatment by coating of a hydrophilic thin film or conducting a surface treatment to the fluid channel 110, the use of a plastic material such as glass can be avoided, and damage to the living body due to mechanical breakage due to pressure load or deformation on the device can be reduced.

Upon contact with the body fluid collection port 102, the body fluid may flow into the fluid channel 110 by the surface tension. The body fluid may be sucked into the fluid channel 110 by a reduced pressure or a negative pressure in the fluid channel 110.

As shown in FIG. 1, in some embodiments, a liquid absorber (liquid absorbing body) 112 may be disposed in at least a portion of the fluid channel 110 that fluidly connects the body fluid collection port 102 to the sensing unit 20.

The liquid absorber 112 may be a material such as a fibrous material, a porous material, a polymer or the like. The liquid absorber 112 may be formed of a hydrophilic material, or may be, for example, a hydrophilic polymer.

When the liquid absorber 112 is disposed, the surface of the channel 110 may be hydrophobic.

The liquid absorber 112 can improve the efficiency of the transport of the liquid in the fluid channel 110. The liquid absorber 112 can increase, for example, an inflow rate of liquid into the fluid channel 110, a suction rate into the fluid channel 110, and a collection rate of body fluid, thereby reducing time for collecting or sampling body fluid. For example, since tears evaporate in a relatively short time, it is preferable to collect them in a short time. When the inner wall of the fluid channel 110 is hydrophilic, the liquid absorber 112 can come into contact with the body fluid. In particular, this action becomes remarkable specifically when the liquid absorber 112 protrudes from the opening of the body fluid collection port 102. When the inner wall of the fluid channel 110 is hydrophobic, the body fluid does not enter the channel 110 without the liquid absorber 112. Therefore, contact with the body fluid becomes efficient by the liquid absorbent body 112, allowing liquid delivery to the channel 110 and increasing the inflow rate.

As shown in FIG. 1, in some embodiments, the fluid collection unit 10 and the sensing unit 20 may be configured to define a liquid containing portion (liquid container) 120. In the example shown in FIG. 1, the sensing unit 20 includes a substrate 200, an electrochemical electrode 212, an output terminal 214, and a wiring 216. The substrate 200 has a first surface 202, a second surface 204, and a side surface 206. The electrochemical electrode 212, the output terminal 214, and the wiring 216 are formed on the first surface 202. The second surface 204 is located on the opposite side of the first surface 202. The side surface 206 is located between the first surface 202 and the second surface 204. The body fluid collection unit 10 covers a portion of the first surface 202 of the substrate 200 and the side surface 206 of the substrate 200. The liquid container 120 overlaps the electrochemical electrode 212 and is connected to the fluid channel 110.

As shown in FIG. 1, in some embodiments, an air hole 130 may be formed in the body fluid collection unit 10. The air hole 130 overlaps with the liquid container 120.

Electrochemical electrode 212 is configured to contact body fluids. Output terminal 214 outputs an electrical signal generated by the electrochemical electrode 212. The wiring 216 connects the electrochemical electrode 212 and the output terminal 214.

The electrochemical electrode 212 may be an electrode for a three-electrode method, or may be an electrode used for other electrochemical measurements.

The electrodes may include a plurality of electrodes, or may be two or three electrodes. In some embodiments, the electrode has two electrodes, and the two electrodes may be a working electrode and a reference electrode used for electrochemical measurements. In other embodiments, the electrode has three electrodes, and the three electrodes may be a working electrode, a reference electrode and a counter electrode.

The electrodes may comprise a plurality of electrode groups. Each electrode group may include a plurality of electrodes.

As shown in FIGS. 4 to 9 which will be explained below, in some embodiments, the sensor chip 30 (sensor) may include a counter electrode 212a configured to contact the solution, a reference electrode 212b configured to contact the solution, and a working electrode 212c configured to contact the solution. In some embodiments, the sensor chip 30 (sensor) may include a counter electrode output terminal 214a for outputting an electrical signal generated at the counter electrode 212a, a reference electrode output terminal 214b for outputting an electrical signal generated at the reference electrode 212b, and a working electrode output terminal 214c for outputting an electrical signal generated at the working electrode 212c. In some embodiments, the sensor chip 30 (sensor) may include a counter electrode wiring 216a connecting the counter electrode 212a and the counter electrode output terminal 214a, a reference electrode wiring 216b connecting the reference electrode 212b and the reference electrode output terminal 214b, and a working electrode wiring 216c connecting the working electrode 212c and the working electrode output terminal 214c.

The surface of the body fluid collection unit 10 or at least a portion of the body fluid collection unit 10 which may come into contact with or come into contact with a solution such as a body fluid collection port 102 or a fluid channel 110 (hereinafter referred to as a cover) may be formed of a biomaterial or a biocompatible material. In some embodiments, the cover may be formed of a biocompatible resin or polymer. In some embodiments, the cover may be formed of a flexible material such as silicone. In some embodiments, the cover may be formed primarily of a hydrophilic material.

In the example shown in FIG. 1, the surface 100 includes a surface 100a, a surface 100b, a surface 100c, a surface 100d, an end 100e, and an end 100f. The surface 100a and the surface 100b are opposed to each other and define a portion of the fluid channel 110. Surface 100c is on the opposite side of surface 100a. Surface 100d is on the opposite side of surface 100b. End 100e is between surface 100a and surface 100c. End 100f is between surface 100b and surface 100d. The surface 100 is configured with a curved surface at a corner from the end 100e to the surface 100a, at a corner from the end 100e to the surface 100c, at a corner from the end 100f to the surface 100b, and at a corner from the end 100f to the surface 100d.

Figure 2:
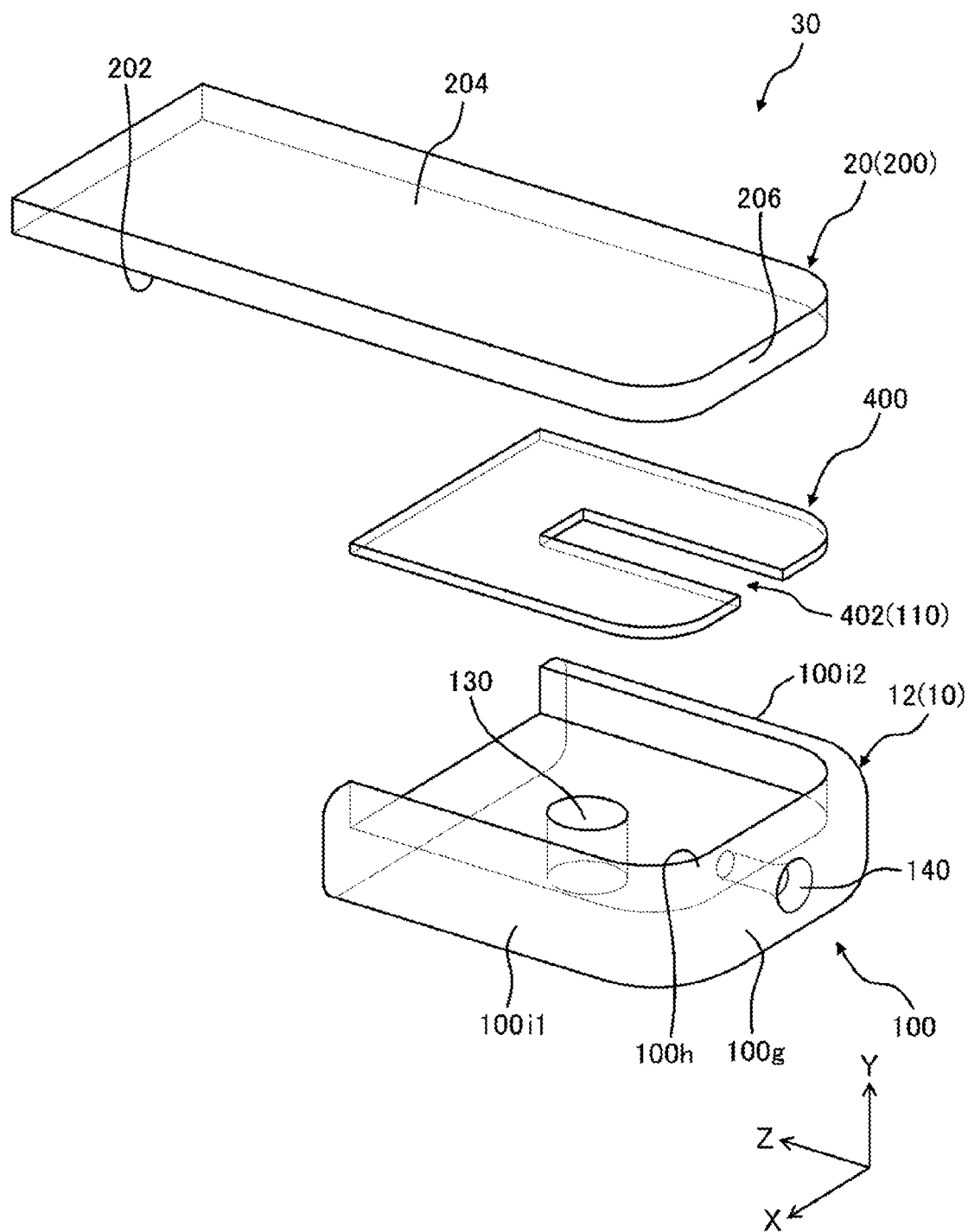
FIG. 2 illustrates an exploded perspective view of a sensor chip and a cover (body fluid collection unit) according to another embodiment.

FIG. 2 illustrates an exploded perspective view of a sensor chip 30 (including a cover 12 and a body fluid collection unit 10) according to another embodiment.

As shown in FIG. 2, in some embodiments, a cover 12 (bodily fluid collection unit 10) may be used on the sensor chip 30. In the example shown in FIG. 2, the sensor chip 30 includes a sensing unit 20 (substrate 200) and a fluid channel unit 400. The fluid channel unit 400 defines a fluid channel 402 (notch). A fluid channel 402 fluidly connects the cover 12 and the sensing unit 20. The fluid channel unit 400 is sandwiched between the cover 12 and the sensing unit 20. The fluid channel 402 corresponds to the fluid channel 110 shown in FIG. 1.

The cover 12 has a surface 100. The surface 100 is formed of a curved surface and comes close to the living body. The surface 100 has a body fluid collection port 102. The cover 12 has a cover fluid channel 140. In the example shown in FIG. 2, the cover fluid channel 140 is formed so as to penetrate the cover 12. The fluid channel 110 is defined by a combination of the sensing unit 20 (200), the fluid channel unit 400, and the cover 12 (10), and is configured to be fluidly connected with the cover flow path 140, or as a part thereof, to fluidly connect the body fluid collection port 102 (FIG. 1) and the electrochemical electrode 212 (FIG. 1) or the containing part 120 (FIG. 1).

In the example shown in FIG. 2, X direction indicates the direction of the width of the cover 12, Y direction indicates the direction of the height of the cover 12, and Z direction indicates the direction of the depth of the cover 12 (the extending direction of the flow path 110).

In the example shown in FIG. 2, the surface 100 includes a surface 100g, a surface 100h, a surface 100i1, and a surface 100i2. The surface 100g faces in a direction along the Z direction. The surface 100h faces in a direction along the Y direction. The surface 100i1 and the surface 100i2 are oriented in opposite directions to each other, along the X direction. The cover 12 is configured with a curved surface at a corner (corner or edge, the same applies hereinafter) from the surface 100g to the surface 100h, at a corner from the surface 100g to the surface 100i1, and at a corner from the surface 100g to the surface 100i2.

Figure 3:
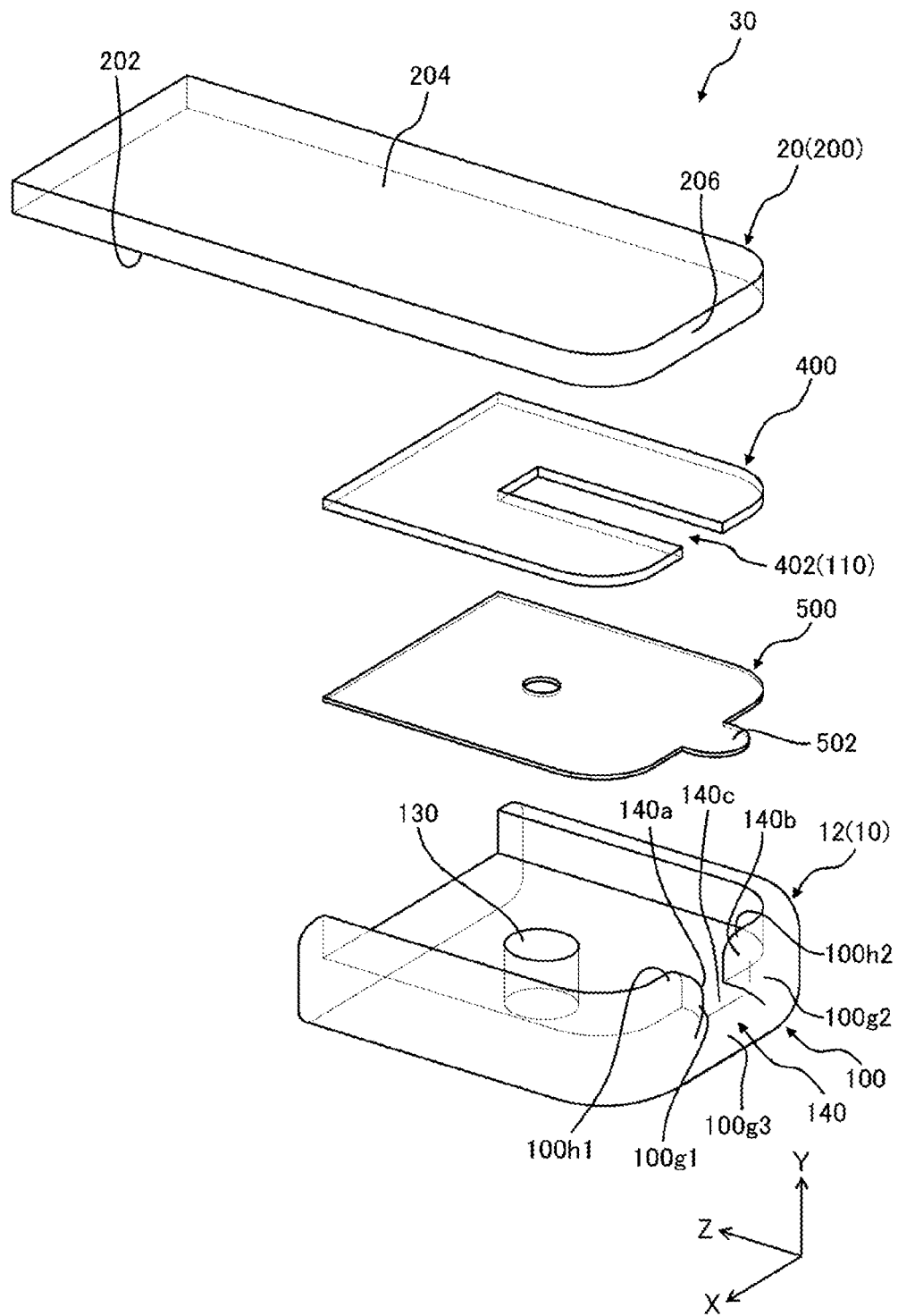
FIG. 3 illustrates an exploded perspective view of a sensor chip and a cover (body fluid collection unit) according to yet another embodiment.

FIG. 3 illustrates an exploded perspective view of a sensor chip 30 (including the cover 12 and the body fluid collection unit 10) according to still another embodiment. The example shown in FIG. 3 illustrates the same as the example shown in FIG. 2 except for the following points.

As shown in FIG. 3, in some embodiments, a lid 500 may be disposed between the cover 12 and the fluid channel unit 400. In the example shown in FIG. 3, the cover fluid channel 140 is formed in a slit shape on the surface of the cover 12. The lid 500 has a protrusion 502. The protrusion 502 penetrates into the cover fluid channel 140. The tip of the protrusion 502 is formed of a curved surface.

In some embodiments, the lid 500 may be formed of a hydrophilic material. When the lid 500 is formed of a hydrophilic material, even if the cover 12 is not formed of a hydrophilic material, body fluid can be easily sent along the fluid channel 402 of the channel unit 400.

In the example shown in FIG. 3, the surface 100 includes a surface 100g1, a surface 100g2, a surface 100g3, a surface 100h1, and a surface 100h2, and the cover fluid channel 140 includes a surface 140a, a surface 140b, and a surface 140c. The surface 100g1 and the surface 100g2 are arranged in the X direction with the cover fluid channel 140 interposed therebetween, and are oriented in a direction along the Z direction. The surface 100h1 and the surface 100h2 are arranged in the X direction with the cover fluid channel 140 interposed therebetween, and are oriented in a direction along the Y direction. The surface 140a and the surface 140b are aligned with each other in the X direction and face each other. The surface 100g3 is aligned with the cover fluid channel 140 in the Y direction, and faces in a direction along the Z direction. The surface 140c is located between the surface 140a and the surface 140b, and faces in a direction along the Y direction. The cover 12 is configured with a curved surface at a corner from the surface 100g1 to the surface 140a, at a corner from the surface 100g2 to the surface 140b, at a corner from the surface 100h1 to the surface 140a, at a corner from the surface 100h2 to the surface 140b, and at a corner from the surface 100g3 to the surface 140c.

In some embodiments, the current flowing to the working electrode during a measurement or the current flowing at the working electrode, required for a measurement, may be less than a value of 1000 nA, 500 nA, 100 nA, 60 nA, 50 nA, 30 nA, 20 nA, 15 nA, 10 nA, 5 nA, and the like.

In some embodiments, the volume of the solution to be measured at the time of measurement, the volume of the solution to be measured, or the container containing the solution may be less than or equal to a value such as 10 µL, 5 µL, 3 µL, 2 µL, 1 µL, 0.5 µL, 0.3 µL, 0.15 µL, and the like.

In general, the current flowing in electrochemical measurements has been as small as 100 nA or 30 nA. At this current level, it was possible to sufficiently reduce the noise by using the existing noise countermeasures.

In particular, if the volume of the solution to be measured becomes small, the problem of noise may become remarkable. To name one example, to name a tear electrochemical measurement, the amount of collected tears is as small as 1 µL or less, and the concentration of, for example, glucose contained in tears is as small as 20-30 µM. Therefore, the volume containing the solution becomes small, and the electrode should therefore be made small. As a result, the current value may be 30 nA or less, or about 20 nA. When performing measurements at such a current level, for example, bringing the dielectric such as a human body close may cause noise on the order from a few nA to 1 nA. This noise level cannot be ignored for the current level.

For example, as a noise countermeasure, a guard may be disposed on both sides of the working electrode or so as to sandwich the working electrode. However, as the size of the container for containing the solution decreases, the contact area of the electrode also decreases. On the other hand, in order to increase the contact area of the electrode as much as possible for sensitivity, it is difficult to take the space other than the electrode. Further, even if it is possible to provide a guard around the wiring, it is difficult to provide a guard around the electrode which is a sensing portion. Therefore, in measurements in which a sensing portion including an electrode is small and a small amount of bodily fluid is used as a target, a noise countermeasure by a conventional guard or the like may not function effectively in some cases.

FIGS. 4 to 9 illustrate diagrams showing first to sixth examples of the layouts of electrodes formed on the first surface 202 of the substrate 200, respectively.

In the examples shown in FIGS. 4 to 9, the counter electrode 212a, the reference electrode 212b, and the working electrode 212c overlap with the liquid containing portion 120.

As shown in FIGS. 4 and 6 to 9, the reference electrode 212b may be disposed between the counter electrode 212a and the working electrode 212c.

The reference electrode 212b is disposed between the counter electrode 212a and the working electrode 212c, so that noise of the electric signals obtained from the electrochemical electrode can be reduced. Since the reference electrode 212b is located between the counter electrode 212a and the working electrode 212c, it is possible to reduce the noise even if the volume is small, which could be reduced by the installation of a guard or the like when the volume was large. The main causes of the noise are external electric field, magnetic field, electromagnetic wave, and static electricity. Thus, it is considered to occur because the reference pole 212b has a higher impedance than the working pole 212c and the counter pole 212a at both ends. It is considered that the counter electrode 212a and the working electrode 212c serve as a guard with respect to the reference electrode 212b. However, the mechanism by which the arrangement of the reference electrode 212b between the counter electrode 212a and the working electrode 212c leads to noise reduction is not limited to the above, or any mechanism can explain as long as other explanations are possible.

Figure 4:
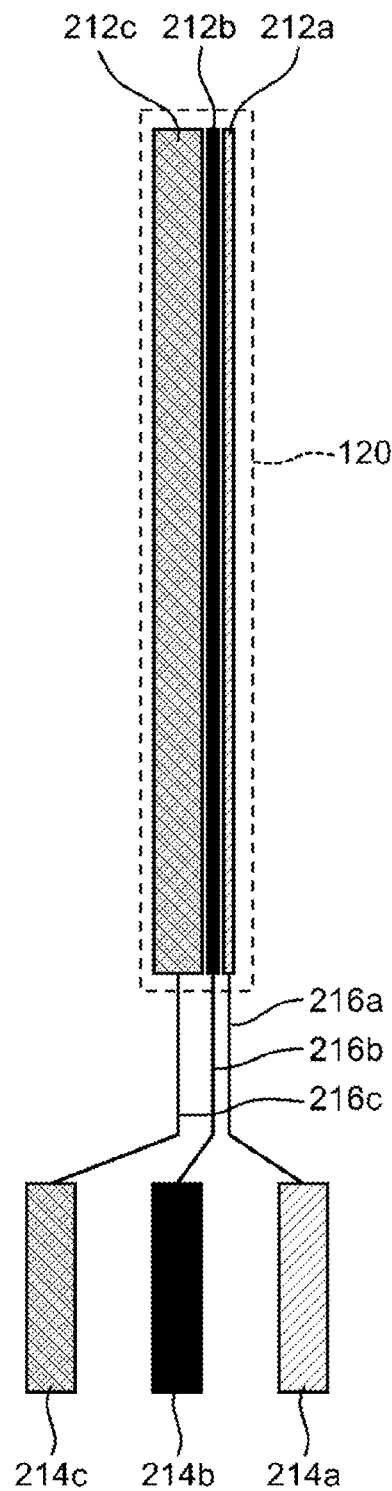
FIG. 4 illustrates a diagram showing a first example of the layout of the electrodes formed on the first surface of the substrate.
Figure 5:
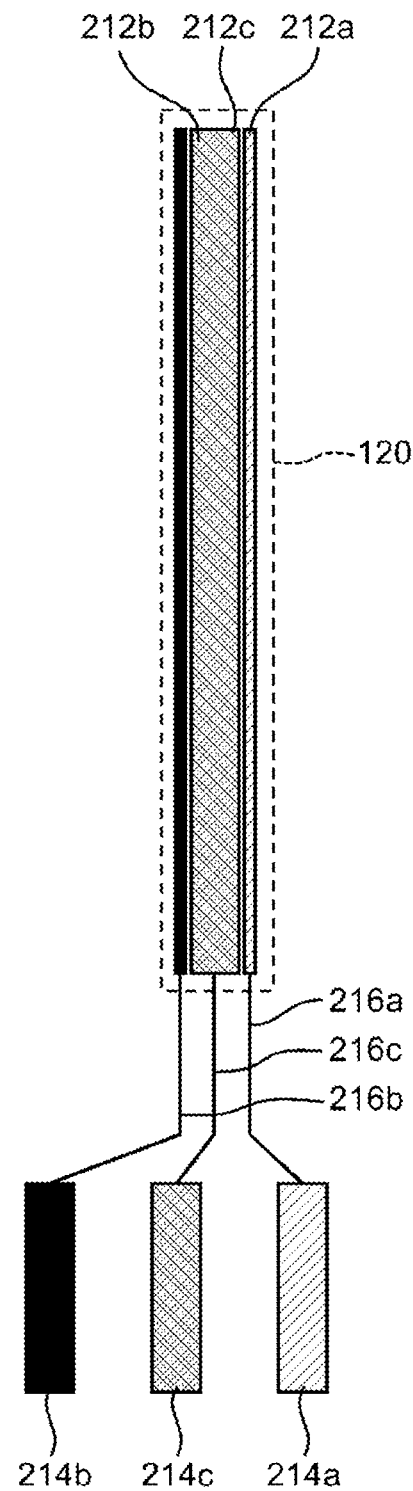
FIG. 5 illustrates a diagram showing a second example of the layout of the electrodes formed on the first surface of the substrate.
Figure 6:
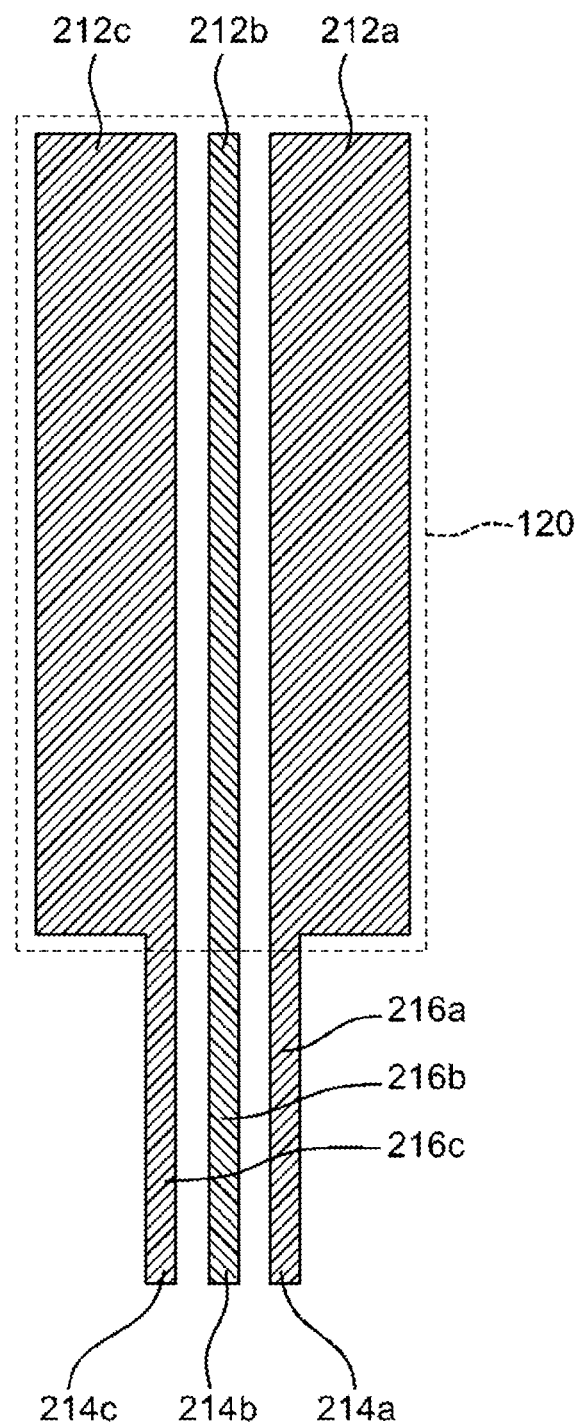
FIG. 6 illustrates a diagram showing a third example of the layout of the electrodes formed on the first surface of the substrate.

As shown in FIGS. 4 to 6, in some embodiments, the counter electrode 212a, the reference electrode 212b, and the working electrode 212c may each be formed (in a linear shape, in a linear type, linear) and disposed parallel to each other.

Figure 7:
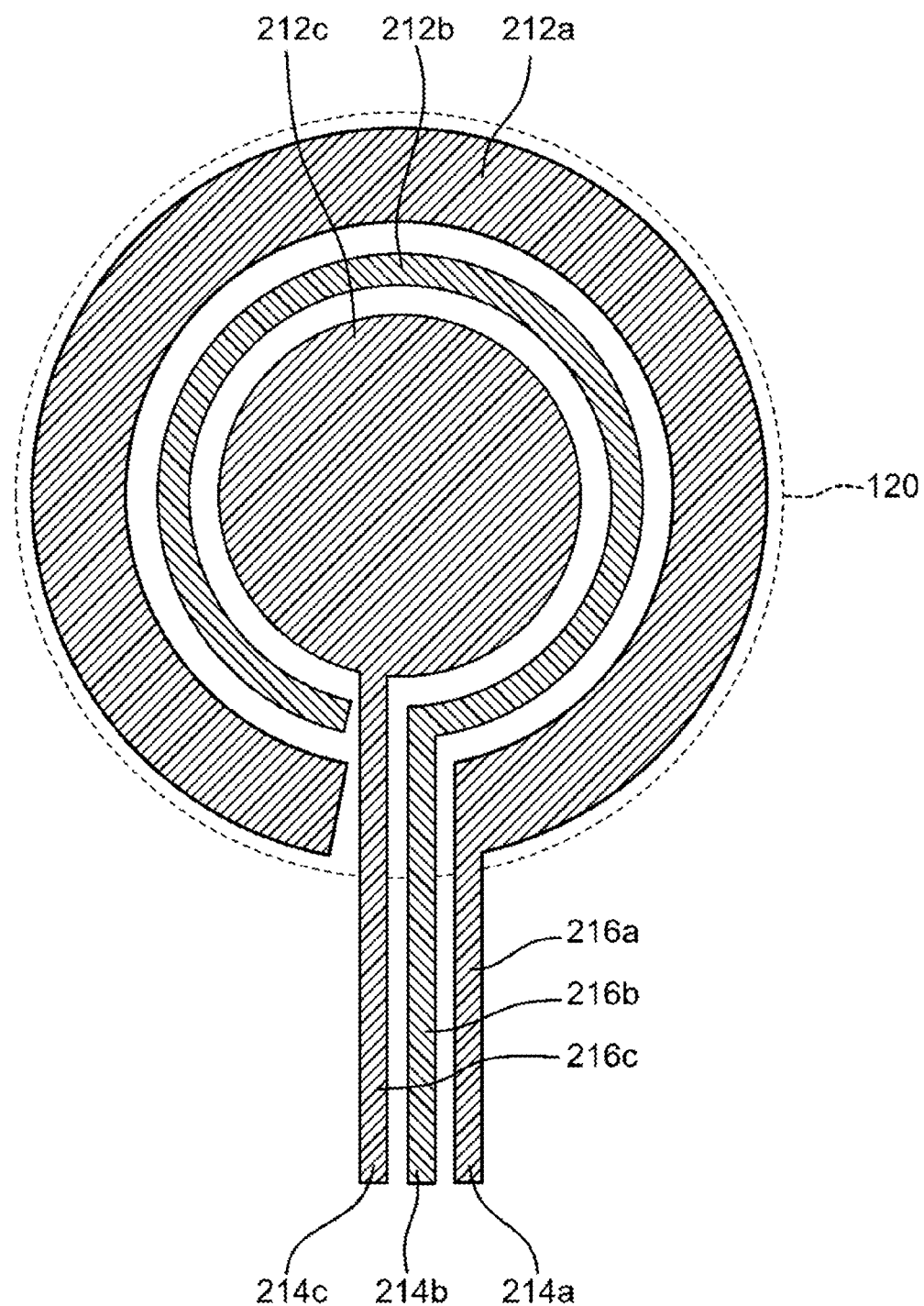
FIG. 7 illustrates a diagram showing a fourth example of the layout of the electrodes formed on the first surface of the substrate.

As shown in FIG. 7, in other embodiments, the counter electrode 212a, the reference electrode 212b, and the working electrode 212c may be arranged substantially concentrically. In the example shown in FIG. 7, the reference electrode 212b surrounds the working electrode 212c, and the counter electrode 212a surrounds the working electrode 212c outside the reference electrode 212b.

Figure 8:
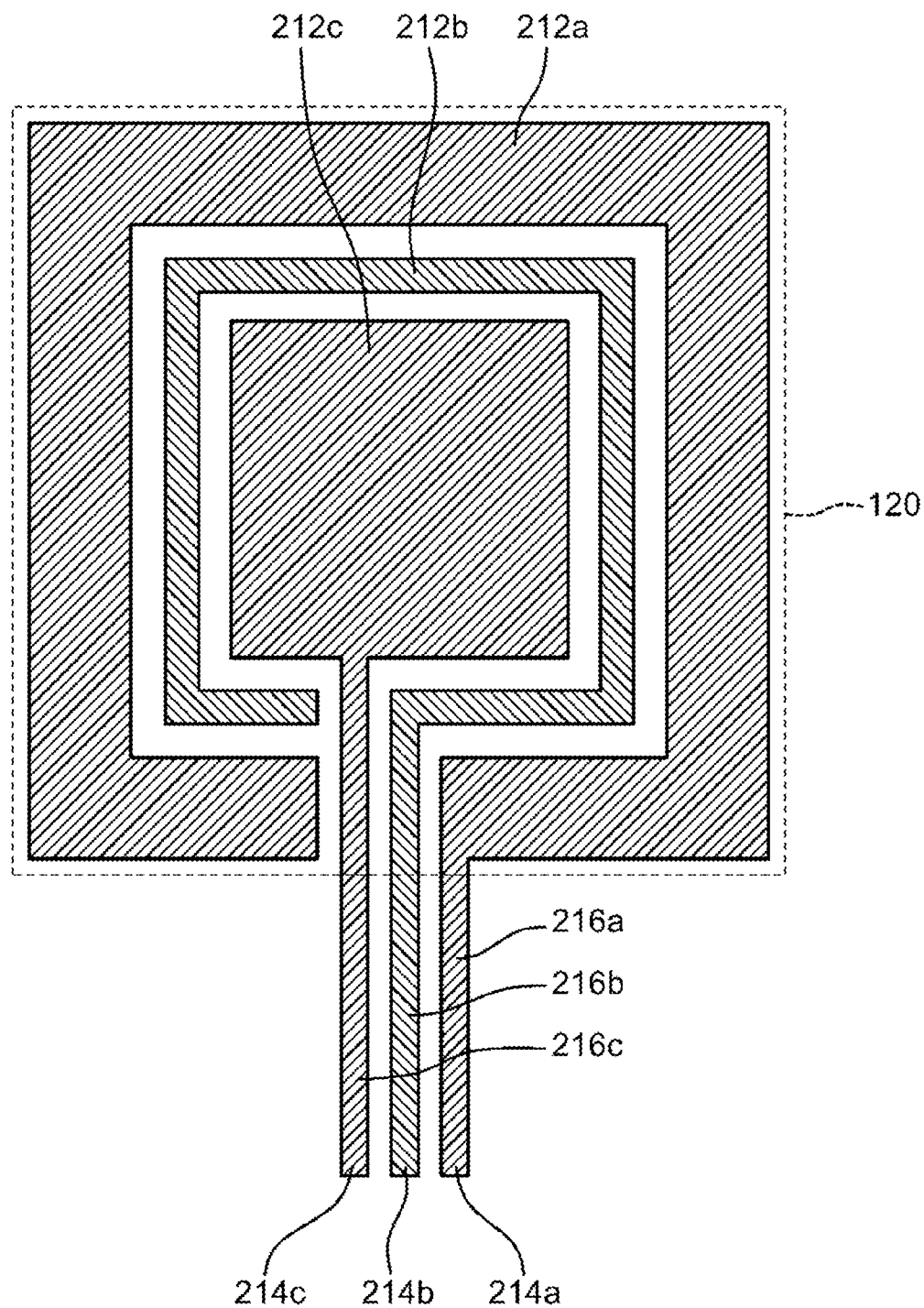
FIG. 8 illustrates a diagram showing a fifth example of the layout of the electrodes formed on the first surface of the substrate.
Figure 9:
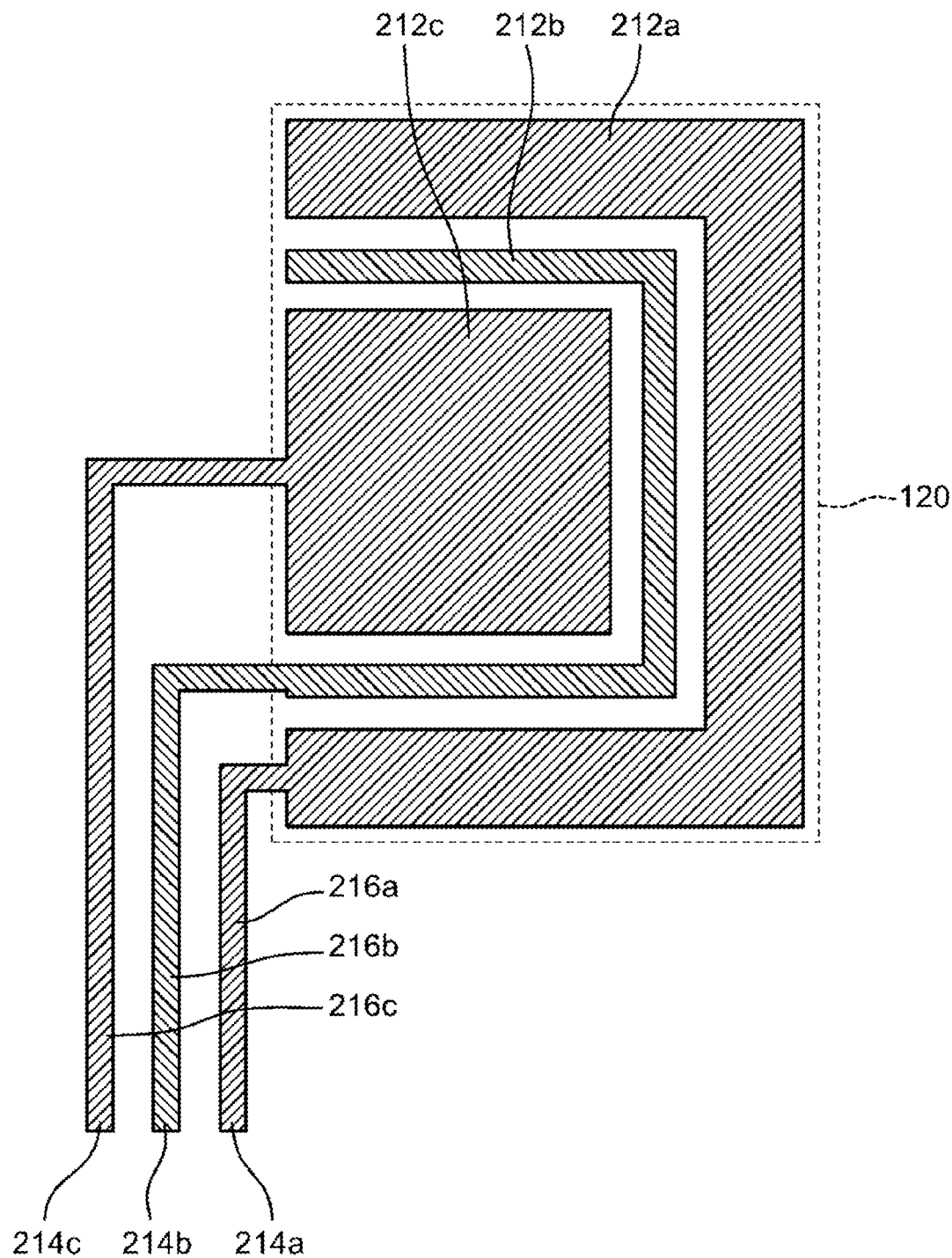
FIG. 9 illustrates a diagram showing a sixth example of the layout of the electrodes formed on the first surface of the substrate.

As shown in FIGS. 8 and 9, in yet another embodiment, the counter electrode 212a, the reference electrode 212b, and the working electrode 212c may be arranged in a substantially concentric polygonal shape. For example, the concentric polygons may be concentric squares, concentric triangles, concentric hexagons, or other concentric N-polygons. In the example shown in FIGS. 8 and 9, the reference electrode 212b surrounds the working electrode 212c, and the counter electrode 212a surrounds the working electrode 212c outside the reference electrode 212b.

In some embodiments, the counter electrode 212a, the reference electrode 212b, and the working electrode 212c may be a single electrode group, and a plurality of electrode groups may be disposed so as to be brought into contact with a body fluid or a solution. The plurality of electrode groups may be composed of the same type of electrode groups, or may be composed of a mixture of different types of electrode groups.

The corners of the electrodes may be rounded. It is considered that electric field concentration is likely to occur at the corners of the electrode, and defects such as film peeling of the electrode during manufacturing, after manufacturing, use, and the like are likely to occur. Therefore, the corners of the electrodes may be formed to have a rounding (R) or curvature.

Figure 10:
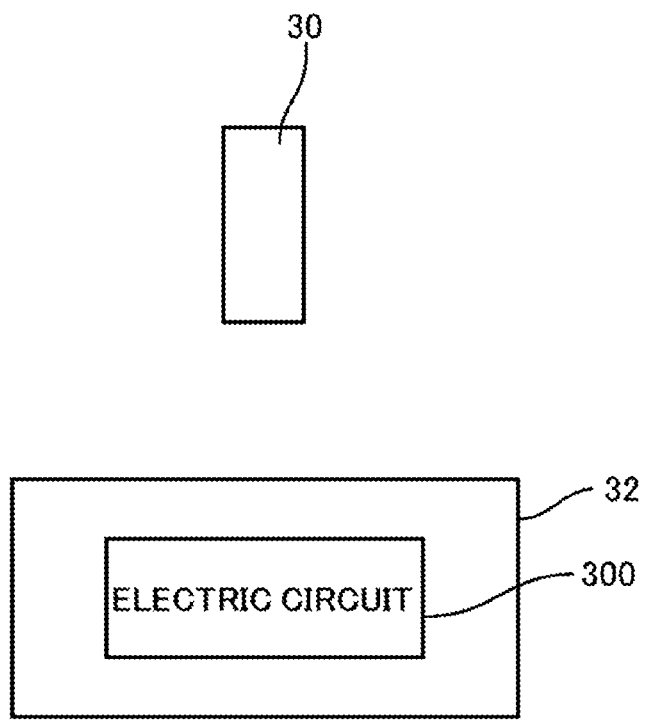
FIG. 10 illustrates a diagram for explaining a method of attaching the sensor chip to the sensor device main body.

FIG. 10 illustrates a diagram for explaining a method of attaching the sensor chip 30 to the sensor device main body 32.

As shown in FIG. 10, in some embodiments, the sensor chip 30 is configured to be electrically connected to the sensor device body 32. The sensor device main body 32 may be provided with terminals corresponding to each output terminal of the sensor chip 30. The sensor device main body 32 includes an electric circuit 300, and the electric circuit 300 may be provided with terminals corresponding to the output terminals of the sensor chip 30, (for example, the counter electrode output terminal 214a, the reference electrode output terminal 214b, and the working electrode output terminal 214c shown in FIGS. 4 to 9). These terminals are electrically connected to each other, whereby electrical signals from the electrodes (e.g., the counter electrode 212a, the reference electrode 212b, and the working electrode 212c shown in FIGS. 4 to 9) in contact with the body fluid in the sensor chip 30 can be transmitted to the electrical circuit 300.

In some embodiments, the electrical circuit 300 may have a communication unit therein or may be connected or configured to be connected to an external communication unit. The communication unit, not shown, may conduct electrical or optical communication. The communication unit can communicate with other devices, systems, servers, networks, and the like, either wired or wirelessly. For example, a device having a sensor chip and a communication unit may acquire biometric information and communicate the biometric information to an electronic device such as a smart phone using NFC (Near Field Communication, International Standard ISO/IEC18092(NFCIP-1), FeliCa (registered trademark), Bluetooth (registered trademark), or the like, or may communicate the biometric information to a wireless LAN such as Wi-Fi (registered trademark).

Figure 11:
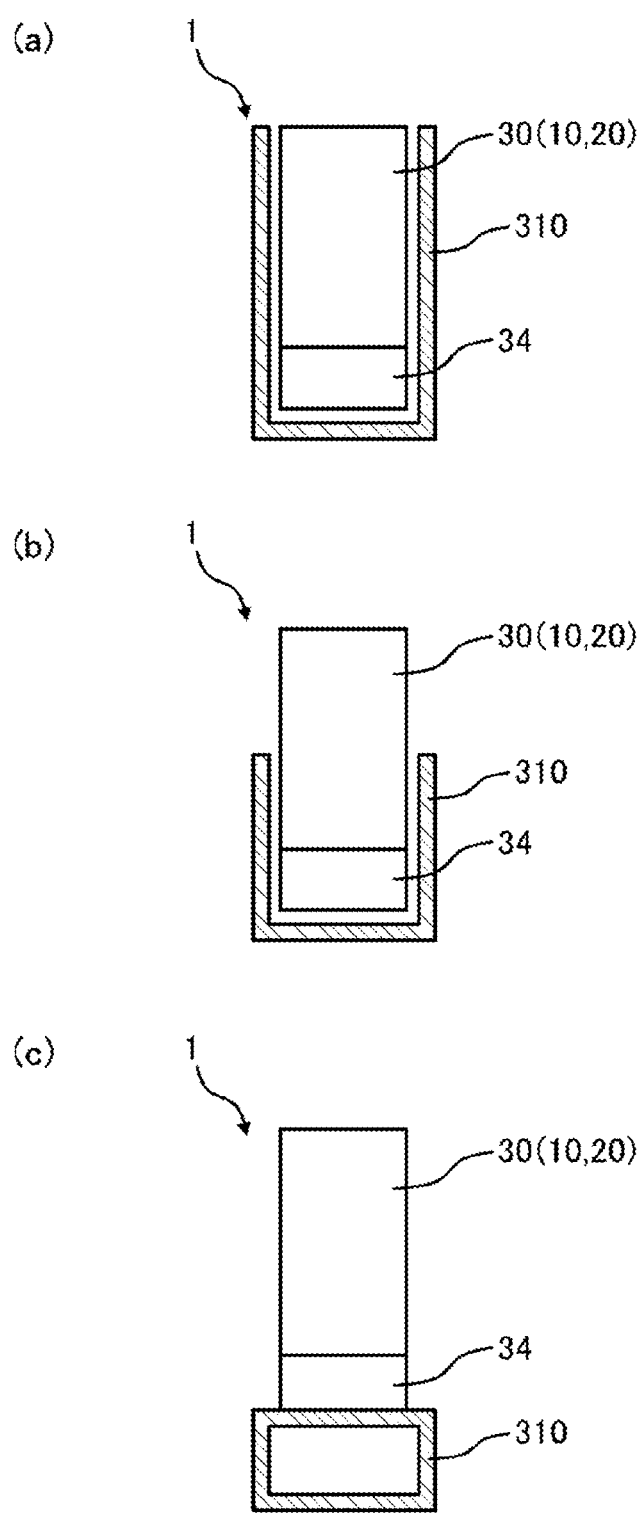
FIG. 11 illustrates a diagram for explaining a sensing device according to an embodiment.

FIG. 11 illustrates a diagram for explaining the sensing device 1 according to an embodiment.

As shown in FIG. 11, in one embodiment, the sensing device 1 includes a sensor chip 30 (the body fluid collection unit 10 and the sensing unit 20), an electric measurement unit 34, and a housing 310. The electrical measuring unit 34 receives an analog signal from the sensing unit 20 and outputs a digital signal.

In another embodiment, the sensing device 1 may not include the housing 310.

As shown in FIG. 11(a), in some embodiments, the housing 310 may house the entire sensor chip 30 and the entire electrical measurement unit 34. As shown in FIG. 11(b), in other embodiments, the housing 310 may house a part of the sensor chip 30 and the electric measurement unit 34. As shown in FIG. 11(c), the housing 310 may not accommodate the sensor chip 30 and the electrical measurement unit 34 at all and may not mechanically connect them. In the examples shown in FIGS. 11(b) and 11(c), the housing 310 may be referred to as a grip portion or a grip.

The body fluid collection unit 10 may be movable relative to the housing 310. The body fluid collection unit 10 may be elastically supported or biased, relative to the housing 310. The body fluid collection unit 10 elastically moves with respect to the housing 310 grasped by the human or the machine when it contacts a living body, thereby reducing the force applied to the living body, and to avoid or reduce the occurrence of problems including damage to the living body. The housing 310 may be a grip portion or grip.

The sensing unit 20 may be fixed relative to the body fluid collection unit 10 or movable relative to the housing 310 along with the body fluid collection unit 10.

EXAMPLES

The following three samples 0T, 1T and 2T were prepared. Each sample was prepared by dissolving glucose in tears taken from humans. The glucose concentrations of the individual samples were measured by high-performance liquid chromatography (HPLC). The glucose levels measured by HPLC are as follows:
0T: 66.8 μM
1T: 116.9 μM
2T: 158.0 μM Each sample was measured by the sensor chip 30 shown in FIG. 3. The layout of the electrodes on the first surface 202 of the substrate 200 was as shown in FIGS. 4 and 6.

Figure 12:
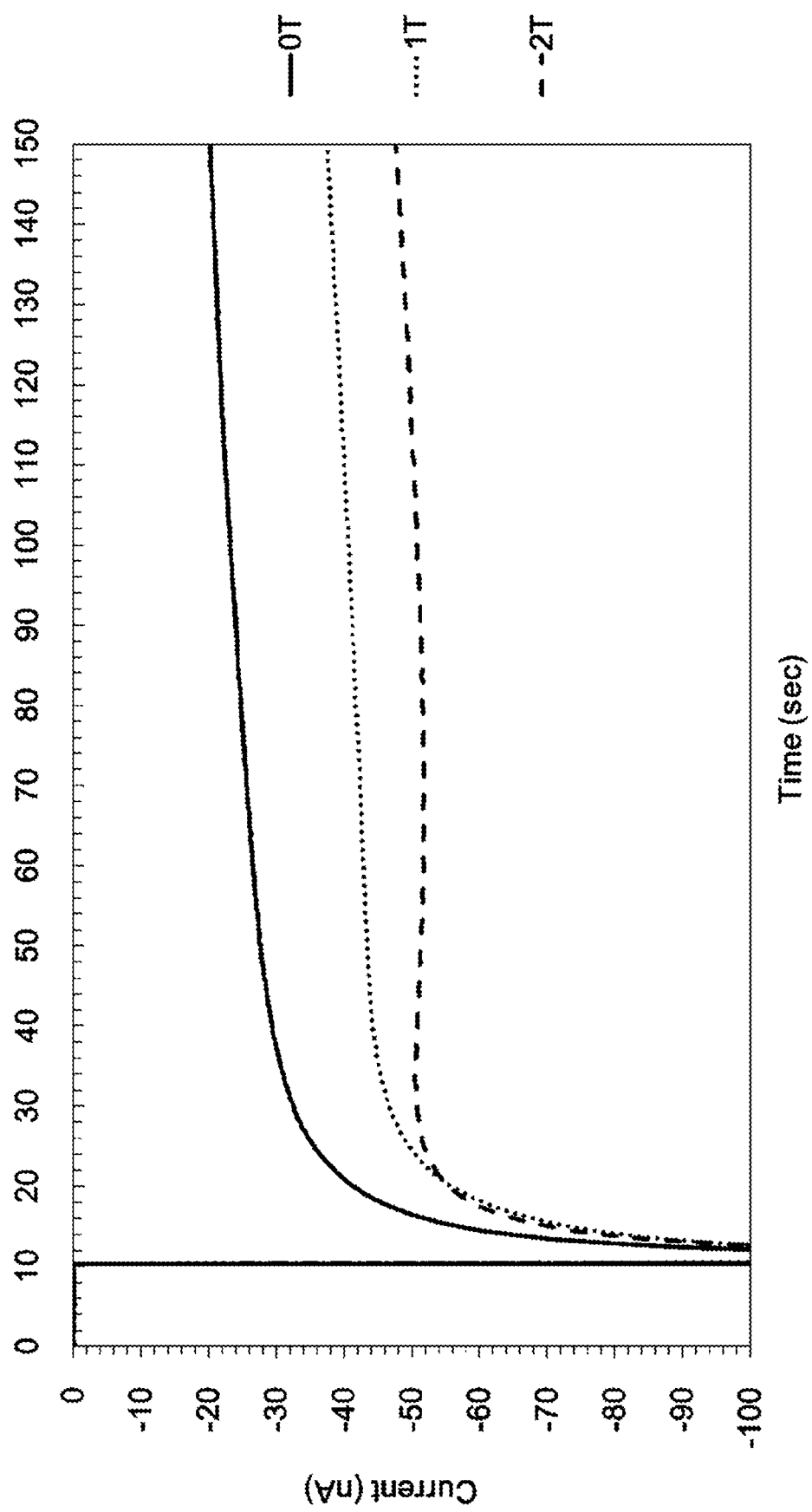
FIG. 12 illustrates a graph showing the output current of a sensor chip.
Figure 13:
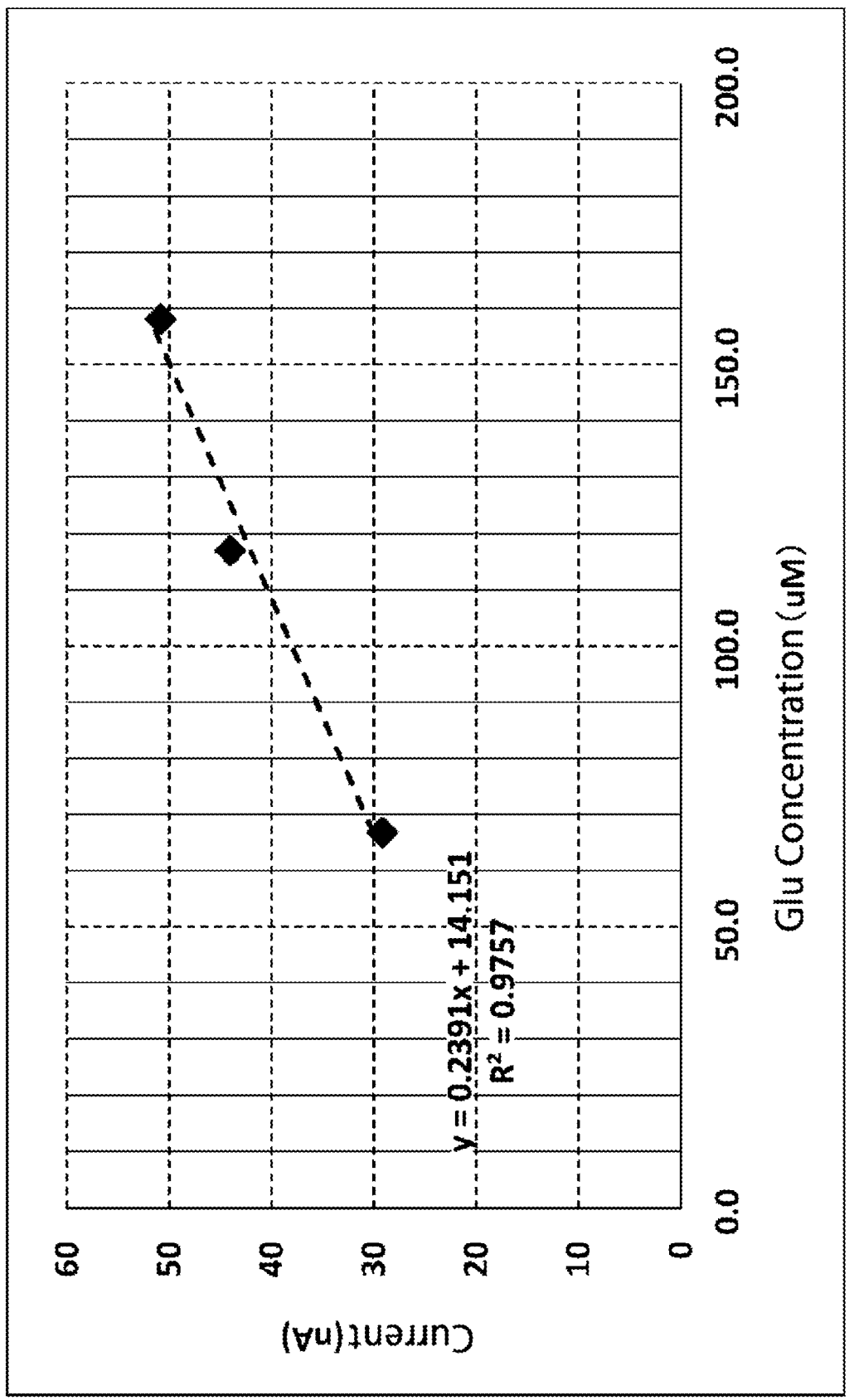
FIG. 13 illustrates a graph showing the relationship between the output current and glucose concentration based on the graph of FIG. 12.

FIG. 12 shows a graph showing the output current of the sensor chip 30. The measurement was started after confirming that the fluid channel 110 of the sensor chip 30 was filled with the sample. Time of 10 seconds in FIG. 12 is the measurement start (voltage application start) time. The output current of the sensor chip 30 was measured by amperometry. FIG. 13 shows a graph showing the relationship between the glucose concentration and the output current at a time point of 40 seconds (30 seconds after the start of measurement) in the graph of FIG. 12.

As shown in FIG. 12, the output current was measured for each of the samples 0T, 1T and 2T from the time point of 10 seconds, that is, from the measurement start time point.

As shown in FIG. 13, a linear correlation of the square R2 of the correlation coefficient of 0.9757 was confirmed between the glucose concentration and the output current of the sensor chip 30. This result suggests that the concentration of glucose contained in tears can be accurately detected by the output current of the sensor chip 30.

Figure 14:
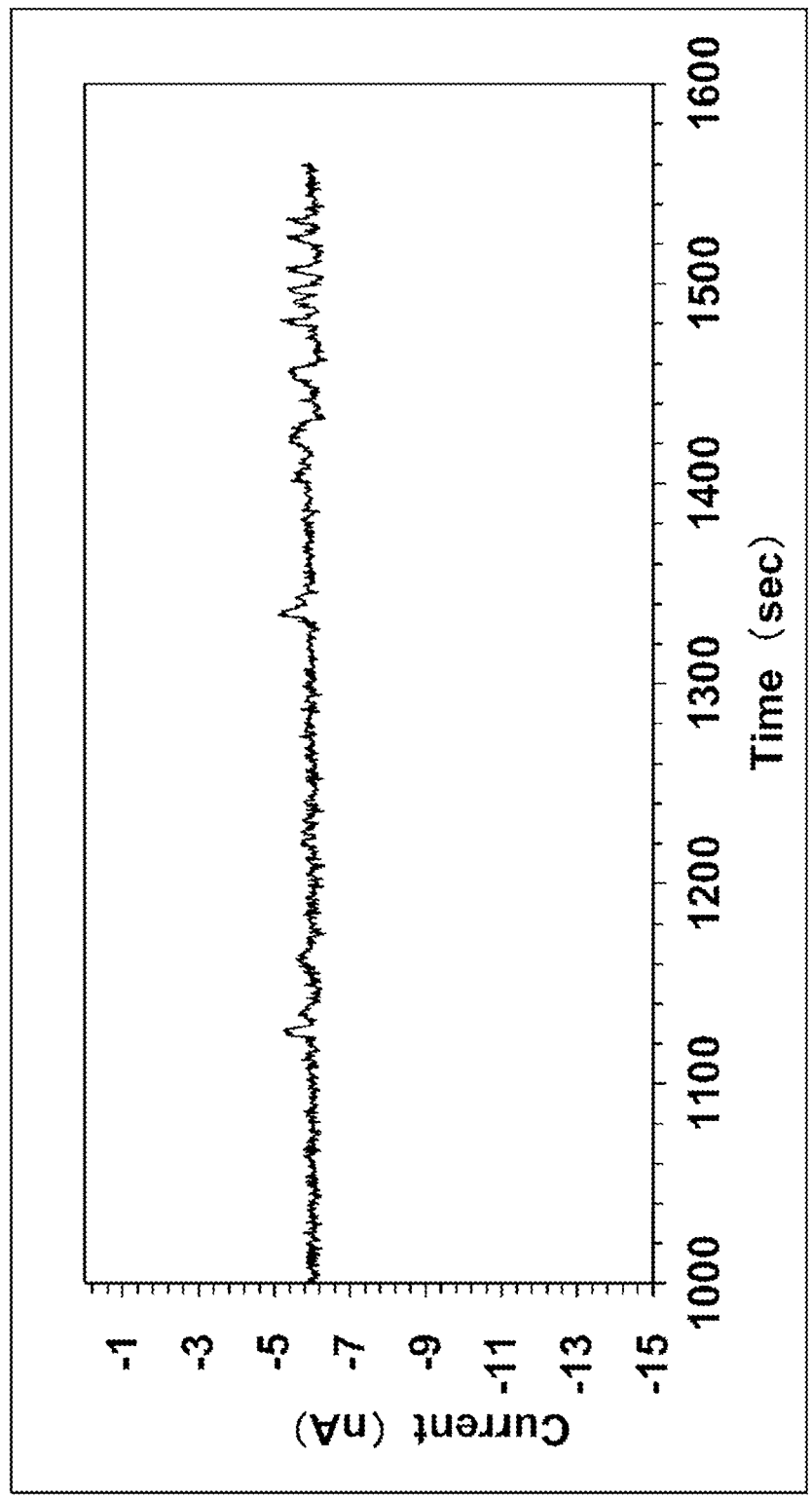
FIG. 14 illustrates a diagram showing a measurement result of the external environment noise by the sensor chip having the layout shown in FIG. 5.
Figure 15:
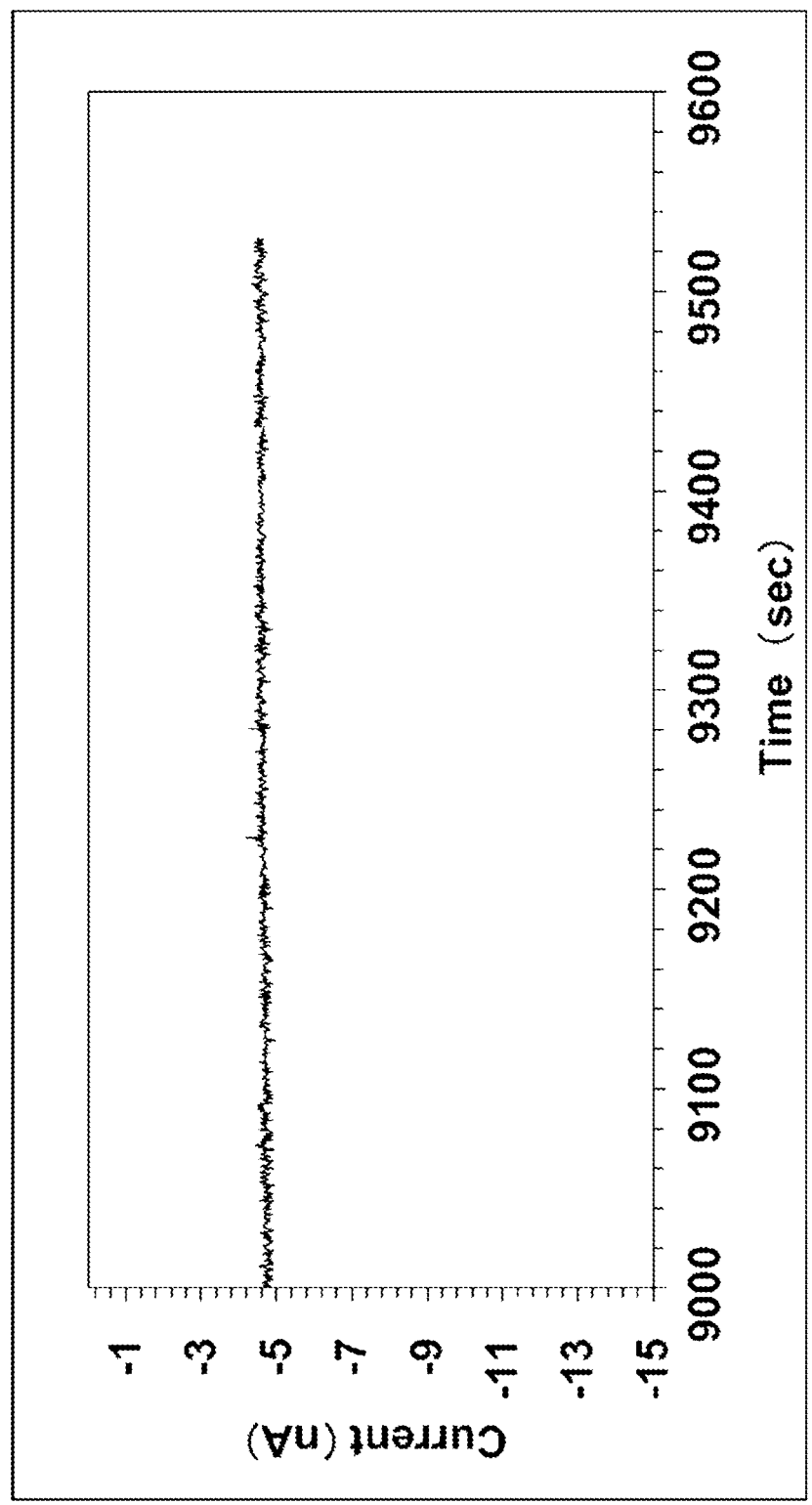
FIG. 15 illustrates a diagram showing a measurement result of the external environment noise by the sensor chip having the layout shown in FIG. 4.

FIG. 14 illustrates a diagram showing a measurement result of the external environment noise by the sensor chip 30 having the layout shown in FIG. 5. FIG. 15 illustrates a diagram showing a measurement result of the external environment noise by the sensor chip 30 having the layout shown in FIG. 4.

In the measurements of FIGS. 14 and 15, the fluid channel 110 of the sensor chip 30 was filled with TES buffer (1 mM TES+150 mM NaCl, pH7), and the output current of the sensor chip 30 was measured by amperometry. In this measurement, external environmental noise was given to the sensor chip 30 by putting a hand over the sensor chip 30.

In the measurement of FIG. 14, as shown in FIG. 5, the reference electrode 212b is not disposed between the counter electrode 212a and the working electrode 212c, and the reference electrode 212b is disposed outside. In the measurement of FIG. 14, noise was confirmed at a time point of about 1100 seconds, a time point of about 1350 seconds, and a time point of about 1500 seconds.

In the measurement of FIG. 15, as shown in FIG. 4, the reference electrode 212b is disposed between the counter electrode 212a and the working electrode 212c, and the reference electrode 212b is disposed inside. In the measurement of FIG. 15, noise having a magnitude equivalent to that of the noise measured in FIG. 14 was not confirmed.

The comparison of the measurement results of FIG. 14 and FIG. 15 indicates that external environmental noise in the sensor chip 30 can be suppressed by arranging the reference electrode 212b between the counter electrode 212a and the working electrode 212c.

The present disclosure includes the following embodiments.

1. A sensor chip to be brought in close proximity to a living body for collecting a body fluid and measuring a chemical substance in the body fluids,
   wherein a surface to be brought in close proximity to the living body is formed by a curved surface.
2. The sensor chip of embodiment 1,
   wherein a curvature of the curved surface is 5 $mm^{-1}$ or less.
3. The sensor chip of embodiment 1 or 2,
   wherein a surface roughness of the curved surface is 1 μmRa or less.
4. The sensor chip of any one of embodiments 1 to 3,
   further comprising a body fluid collection port disposed within the surface to be brought in close proximity to the living body.
5. The sensor chip of embodiment 4,
   wherein an opening of the body fluid collection port is formed with a curved surface,
6. A sensor chip to be brought in close proximity to a living body for collecting a body fluid and measuring a chemical substance in the body fluid, the sensor chip comprising:
   a body fluid collection unit having a surface configured by a curved surface and configured to be brought in close proximity to the living body and having a body fluid collection port for collecting the body fluid; and
   a sensing unit for performing a chemical measurement on the bodily fluid collected by the body fluid collection unit.
7. The sensor chip of embodiment 6,
   wherein the body fluid collection unit and the sensing unit are detachable from each other.
8. The sensor chip of embodiment 6 or 7,
   wherein the body fluid collection unit further comprises a fluid channel fluidly connecting the bodily fluid collection port to the sensing unit.
9. The sensor chip of any one of embodiments 6 to 8, further comprising a fluid channel unit defining a fluid channel fluidly connecting the body fluid collection unit and the sensing unit.
10. The sensor chip of embodiment 8 or 9,
    wherein at least a portion of a surface of the fluid channel is hydrophilic.
11. The sensor chip of any one of embodiments 8 to 10,
    wherein the body fluid, upon contact with the body fluid collection port, flows into the fluid channel by surface tension.
12. The sensor chip of any one of embodiments 8 to 11,
    further comprising a liquid absorber disposed to the fluid channel fluidly connecting the body fluid collection port to the sensing unit.
13. The sensor chip of any one of embodiments 6 to 12, further comprising:
    an electrochemical electrode configured to contact the bodily fluid;
    an output terminal for outputting an electric signal generated by the electrochemical electrode; and
    a wiring for connecting the electrochemical electrode and the output terminal.
14. The sensor chip of embodiment 13,
    wherein the electrochemical electrode comprises an electrode for a three-electrode method.

15. The sensor chip of embodiment 13 or 14,
wherein the sensor chip is configured to be electrically connected to the sensor device body having an electrical circuit.
16. A sensor chip to be brought in close proximity to a living body for collecting a body fluid and performing an electrochemical measurement on the body fluid, the sensor ship comprising:
a body fluid collection unit having a surface configured with a curved surface and configured to be brought in close proximity to the living body and having a body fluid collection port for collecting the body fluid;
a sensing unit for performing an electrochemical measurement on the body fluid collected by the body fluid collection unit; and
an electrical measuring unit for receiving an analog electrical signal from the sensing unit and outputting a digital signal.
17. A sensor chip to be brought in close proximity to a living body for collecting a body fluid and performing an electrochemical measurement on the body fluid, the sensor ship comprising:
a body fluid collection unit having a surface configured with a curved surface and configured to be brought in close proximity to the living body and having a body fluid collection port for collecting the body fluid;
a sensing unit for performing an electrochemical measurement on the body fluid collected by the body fluid collection unit;
an electrical measuring unit for receiving an analog electrical signal from the sensing unit and outputting a digital signal; and
a housing.
18. The sensing device of embodiment 17, wherein the body fluid collection unit is movable relative to the housing.
19. A cover to be brought in close proximity to a living body for collecting a body fluid and performing a chemical measurement on the body fluid, the cover comprising:
a surface configured with a curved surface and to be brought in close proximity to the living body.
20. The cover of embodiment 19, wherein the surface to be brought in close proximity to the living body has a fluid collection port,
the cover further comprising a cover fluid channel configured to fluidly connect the body fluid collection port and the sensor chip by combining the sensor chip and the cover.
21. The cover of embodiment 20, wherein the cover fluid channel is formed to penetrate the cover.
22. The cover of embodiment 20, wherein the cover fluid channel is formed in a slit shape on a surface of the cover.
23. The cover of any one of embodiments 19 to 22, mainly made of a hydrophilic material.
24. A body fluid collection device to be brought in close proximity to a living body for collecting a body fluid, wherein the surface to be brought in close proximity to the living body is configured with a curved surface.
25. A sensor for electrochemical measurement of a liquid, comprising:
a counter electrode configured to contact the liquid;
a working electrode configured to contact the liquid; and
a reference electrode configured to contact the liquid and disposed between the counter electrode and the working electrode.
26. The sensor of embodiment 25, wherein the counter electrode, the reference electrode, and the working electrode are arranged linearly and parallel to each other.
27. The sensor of embodiment 25, wherein the counter electrode, the reference electrode and the working electrode are arranged substantially concentrically.
28. The sensor of embodiment 25, wherein the counter electrode, the reference electrode and the working electrode are arranged in a substantially concentric polygonal shape.

While several embodiments and examples of the present disclosure have been described above, these embodiments and examples explain the present disclosure in exemplary manners. For example, each of the above-described embodiments has been described in detail in order to explain the present invention in a way easy to understand, and a circuit may be added as necessary. It is intended that the claims cover numerous modifications to the embodiments without departing from the spirit and scope of the present disclosure. Accordingly, the embodiments and examples disclosed herein have been shown by way of illustration and should not be considered as limiting the scope of the present disclosure.

This application claims priority to Japanese Patent Application No. 2018-067742, filed Mar. 30, 2018, the entire disclosure of which is incorporated herein by reference.

The invention claimed is:
1. A sensor chip to be brought in close proximity to a living body for collecting a body fluid and measuring a chemical substance in the body fluid, the sensor chip comprising:
a body fluid collection unit comprising a body fluid collection port and an opening of the body fluid collection port, the body fluid collection port having a surface comprising a first curved surface and a second curved surface, wherein the first curved surface and the second curved surface are surfaces other than the opening and configured to be brought in close proximity to the living body, wherein the opening of the body fluid collection port is configured by the second curved surface, wherein the curvature of the first curved surface and the curvature of the second curved surface are continuous; and wherein the first curved surface and the second curved surface have the same radius of curvature that is 0.5 mm or greater; and
a sensing unit for performing a chemical measurement on the bodily fluid collected by the body fluid collection unit; and
a fluid channel unit defining a fluid channel fluidly connecting the body fluid collection unit and the sensing unit.
2. The sensor chip of claim 1,
wherein the body fluid collection unit and the sensing unit are detachable from each other.
3. The sensor chip of claim 1,
wherein the body fluid collection unit further comprises a fluid channel fluidly connecting the bodily fluid collection port to the sensing unit.
4. The sensor chip of claim 3,
wherein at least a portion of a surface of the fluid channel is hydrophilic.
5. The sensor chip of claim 3,
wherein the body fluid, upon contact with the body fluid collection port, flows into the fluid channel by surface tension.
6. The sensor chip of claim 3, further comprising a liquid absorber disposed to the fluid channel fluidly connecting the body fluid collection port to the sensing unit.

7. The sensor chip of claim 1, further comprising:
an electrochemical electrode configured to contact the bodily fluid;
an output terminal for outputting an electric signal generated by the electrochemical electrode; and
a wiring for connecting the electrochemical electrode and the output terminal.

8. The sensor chip of claim 7, wherein the electrochemical electrode comprises an electrode for a three-electrode method.

9. The sensor chip of claim 7,
wherein the sensor chip is configured to be electrically connected to a sensor device body having an electrical circuit.

* * * * *